(12) United States Patent
Fujiwara et al.

(10) Patent No.: US 12,051,340 B2
(45) Date of Patent: Jul. 30, 2024

(54) CONTENT CREATION SYSTEM

(71) Applicant: Hitachi Systems, Ltd., Tokyo (JP)

(72) Inventors: Takayuki Fujiwara, Tokyo (JP);
Shintaro Tsuchiya, Tokyo (JP);
Kentarou Oonishi, Tokyo (JP);
Katsuro Kikuchi, Tokyo (JP);
Yoshihito Narita, Tokyo (JP)

(73) Assignee: Hitachi Systems, Ltd., Tokyo (JP)

( * ) Notice: Subject to any disclaimer, the term of this patent is extended or adjusted under 35 U.S.C. 154(b) by 0 days.

(21) Appl. No.: 16/626,014

(22) PCT Filed: Aug. 24, 2018

(86) PCT No.: PCT/JP2018/031352
§ 371 (c)(1),
(2) Date: Dec. 23, 2019

(87) PCT Pub. No.: WO2020/003545
PCT Pub. Date: Jan. 2, 2020

(65) Prior Publication Data
US 2022/0051579 A1 Feb. 17, 2022

(30) Foreign Application Priority Data
Jun. 29, 2018 (JP) ................................ 2018-124688

(51) Int. Cl.
*G09B 5/06* (2006.01)
*G06Q 10/067* (2023.01)
(Continued)

(52) U.S. Cl.
CPC ........... *G09B 5/065* (2013.01); *G06Q 10/067* (2013.01); *G09B 19/003* (2013.01); *G09B 19/24* (2013.01)

(58) Field of Classification Search
CPC .................................................... G09B 19/24
See application file for complete search history.

(56) References Cited

U.S. PATENT DOCUMENTS 8,512,043 B2 * 8/2013 Choquet ............ A63B 24/0021
434/234
9,318,026 B2 * 4/2016 Peters ...................... G09B 5/02
(Continued)

FOREIGN PATENT DOCUMENTS

CN 107331220 A 11/2017
JP 2003-167613 A 6/2003
(Continued)

OTHER PUBLICATIONS

Database WPI Week 201779, Thomson Scientific, London, GB; AN2017-778293 XP002801126.
(Continued)

*Primary Examiner* — Kang Hu
*Assistant Examiner* — Correll T French
(74) *Attorney, Agent, or Firm* — Venable LLP; Henry J. Daley

(57) ABSTRACT

The content creation system comprises: an operation measurement device 1 that acquires, as measurement information, a three-dimensional work operation of a model worker R1 that performs the work of the work procedure; an evaluation criterion creation device 2 that creates evaluation criterion information on the work of the work procedure, based on the measurement information of the three-dimensional work operation; and a content creation device 3 that creates and updates the training content, based on the measurement information of the three-dimensional work operation, the evaluation criterion information and the three-dimensional shape information of the work target device. The work management server 2 creates the evaluation criterion information, based on distance information of the three-dimensional work operation with respect to the three-dimensional shape in specific stage of the work procedure, (Continued)

on the condition that a predetermined body motion of the model worker R1 is detected.

11 Claims, 13 Drawing Sheets

(51) Int. Cl.
   *G09B 19/00* (2006.01)
   *G09B 19/24* (2006.01)

(56) References Cited

U.S. PATENT DOCUMENTS

| | | | | |
|---|---|---|---|---|
| 9,368,045 | B2* | 6/2016 | Becker | G09B 9/00 |
| 9,911,351 | B2* | 3/2018 | White | G06F 3/017 |
| 10,403,046 | B2* | 9/2019 | Pinti | G06F 3/011 |
| 2002/0123812 | A1* | 9/2002 | Jayaram | G06T 19/20 |
| | | | | 700/98 |
| 2007/0048702 | A1* | 3/2007 | Jang | G09B 19/00 |
| | | | | 434/224 |
| 2008/0038702 | A1* | 2/2008 | Choquet | G09B 19/0038 |
| | | | | 434/260 |
| 2008/0124698 | A1* | 5/2008 | Ebensberger | G09B 11/10 |
| | | | | 434/365 |
| 2009/0298024 | A1* | 12/2009 | Batzler | G09B 19/003 |
| | | | | 434/234 |
| 2010/0048273 | A1* | 2/2010 | Wallace | G09B 9/00 |
| | | | | 463/7 |
| 2013/0189656 | A1* | 7/2013 | Zboray | G06F 3/012 |
| | | | | 434/219 |
| 2013/0285909 | A1* | 10/2013 | Patel | G09B 5/00 |
| | | | | 345/158 |
| 2015/0050623 | A1* | 2/2015 | Falash | G09B 9/24 |
| | | | | 434/362 |
| 2015/0056584 | A1* | 2/2015 | Boulware | B23K 9/32 |
| | | | | 434/234 |
| 2015/0147734 | A1* | 5/2015 | Flores | G09B 19/0015 |
| | | | | 434/247 |
| 2016/0371174 | A1 | 12/2016 | Ikeda | |
| 2017/0124338 | A1 | 5/2017 | Oonishi et al. | |
| 2017/0132554 | A1 | 5/2017 | Oonishi et al. | |
| 2017/0358243 | A1* | 12/2017 | Kim | G09B 19/0038 |
| 2018/0374026 | A1 | 12/2018 | Osawa et al. | |
| 2019/0239850 | A1* | 8/2019 | Dalvin | A61B 8/462 |
| 2019/0362243 | A1 | 11/2019 | Matsumura | |
| 2019/0392728 | A1* | 12/2019 | Pike | G06T 19/003 |
| 2020/0273365 | A1* | 8/2020 | Wallace | G06F 3/016 |

FOREIGN PATENT DOCUMENTS

| | | |
|---|---|---|
| JP | 2011-164694 A | 8/2011 |
| JP | 2018-10630 A | 1/2018 |
| JP | 6321879 B1 | 5/2018 |
| JP | 2019-109844 A | 7/2019 |
| WO | 2015/189994 A1 | 12/2015 |
| WO | 2016/002056 A1 | 1/2016 |
| WO | 2017/014733 A1 | 1/2017 |
| WO | 2017/119127 A1 | 7/2017 |

OTHER PUBLICATIONS

EP Application No. 22201336.9 European Search Report dated Jan. 20, 2023.

* cited by examiner

| Index | Execution Date | Start Time | Finish Time | Applicable Task | Work Result |
|---|---|---|---|---|---|
| 1 | 20180330 | 14:10 | 14:20 | Air Conditioner Electric Circuit Exchange | Completed |
| 2 | 20180330 | 14:25 | | Air Conditioner Centralized Controller Substrate Exchange | In Progress |
| 3 | 20180330 | | | Air Conditioner Centralized Controller Wiring Inspection | Not Executed |
| 4 | 20180330 | | | | |
| 7 | ... | ... | ... | ... | ... |

FIG.6

| Index | Task | Procedure | Contents Data Material |
|---|---|---|---|
| 1 | Air Conditioner Electric Circuit Exchange | Confirm Target | item.jpg, item.fbx, manual_1.txt |
| 2 | | Open Cover | Cover.jpg, cover.fbx, instruction_2.mp4, manual_2.txt |
| 3 | | Remove Circuit | electronic_circuit.jpg, electronic_circuit.fbx, instruction_3.mp4, manual_3.txt, |
| 4 | | Attach Circuit | electronic_circuit.jpg, electronic_circuit.fbx, instruction_4.mp4, manual_4.txt, |
| 5 | | Attach Cover | Cover.jpg, cover.fbx, instruction_5.mp4, manual_5.txt |
| 6 | | Confirm No Problem in Operation | Item.jpg, item.fbx, manual_6.txt |
| ... | ... | ... | ... |

FIG.7

| Index | Execution Date | Sight Line Variation | Arm Operation Variation | Feature Point Variation | Video |
|---|---|---|---|---|---|
| 1 | 20180330 | 20180330_141003_start_eye.csv | 20180330_141003_start_arm.csv | 20180330_141003_start_featurepoint.csv | 20180330_141003_start.mp4 |
| 2 | 20180330 | 20180330_141209_start_eye.csv | 20180330_141209_start_arm.csv | 20180330_141209_start_featurepoint.csv | 20180330_141209_start.mp4 |
| 3 | 20180330 | 20180330_141412_start_eye.csv | 20180330_141412_start_arm.csv | 20180330_141412_start_featurepoint.csv | 20180330_141412_start.mp4 |
| 4 | 20180330 | 20180330_141605_start_eye.csv | 20180330_141605_start_arm.csv | 20180330_141605_start_featurepoint.csv | 20180330_141605_start.mp4 |
| 5 | 20180330 | 20180330_141742_start_eye.csv | 20180330_141742_start_arm.csv | 20180330_141742_start_featurepoint.csv | 20180330_141742_start.mp4 |
| 6 | 20180330 | 20180330_141805_start_eye.csv | 20180330_141805_start_arm.csv | 20180330_141805_start_featurepoint.csv | 20180330_141805_start.mp4 |
| ... | ... | ... | ... | ... | ... |

FIG.8

Training Starts.
Please Install Necessary Sensors.

Return

FIG.12A

CONTENT CREATION SYSTEM

This application is a National Stage Application under 35 U.S.C. § 371 PCT/JP2018/031352, filed Aug. 24, 2018, which claims priority benefit from Japanese patent application no. 2018/124668, filed on Jun. 29, 2018, the entire content of which is incorporated herein by reference. All references cited anywhere in this specification, including the Background and Detailed Description sections, are incorporated by reference as if each had been individually incorporated.

FIELD OF THE INVENTION

The present invention relates to a content creation system, and specifically relates to a content creation system for creating training content including 3D CG for performing a simulated work.

BACKGROUND ART

Systems for presenting training content with videos and voices that support a work of a worker are known as work support systems, a typical one of which transfers the training content from a management server to the worker who performs maintenance work or the like while having the worker wear or carry an information terminal capable of acquiring videos or sounds.

Such content that serves as work support information is usually created based on a manual describing work procedure, notes, and the like. Conventionally, such content that rules the determination condition of work target and work situation by associating, for example, the terms, headings, items, tables, figures, images and other elements included in the manual is known (see, for example, Patent Document 1).

In this case, the work support system recognizes a work target and a work situation based on sensor information from an information terminal device on the worker side in accordance with the above-mentioned rule, and transmits the work support information corresponding to the recognition result to the information terminal device on the worker side.

CITATION LIST

Patent Literature

Patent Document 1: Japanese Patent No. 6321879

SUMMARY OF THE INVENTION

Technical Problem

However, in the work support systems for creating content as described above, in the case where it is desired to manually make an exemplary work operation of experts concerning maintenance work etc. of a device not equipped with a manual, it is necessary for creating manual content to grasp important information on the work from an interview to the experts, photographs of the work target and workers, images for explanation of the work operation, etc., so that it takes man-hours to create the content.

In addition, although it is possible to use the work support system as a training system that allows the worker to perform a simulated work to acquire and master the maintenance work, etc., in such a case, it has not been accomplished to appropriately incorporate experts' know-how and notes or criterion to evaluate the results of that training in the training manual.

The present invention has been made to solve the conventional problem as described above, and for the purpose of providing a content creation system capable of: easily and reliably reflecting an important work operation and evaluation criterion among model work by experts and the like to the training content for supporting the work: contributing to the reduction of man-hours for creation of the content; and creating content that can be effectively utilized for evaluating the training result.

Means to Solve the Problem

In order to achieve the above object, the content creation system according to the present invention is a content creation system that creates training content based on three-dimensional shape information of a work target device and a work procedure to a trainee to have executed a simulated work of virtual reality or augmented reality, the content creation system comprising: an operation measurement device that acquires, as measurement information, a three-dimensional work operation of a model worker that performs the simulated work of the work procedure: an evaluation criterion creation device that creates evaluation criterion information on the simulated work of the work procedure, based on the measurement information of the three-dimensional work operation; and a content creation device that creates and updates the training content, based on the measurement information of the three-dimensional work operation, the evaluation criterion information and three-dimensional shape information of the work target device, wherein the evaluation criterion creation device creates the evaluation criterion information, based on distance information of the three-dimensional work operation with respect to the three-dimensional shape in specific stage of the work procedure, on the condition that a predetermined body motion of the model worker is detected.

By this configuration, according to the present invention, when a predetermined body motion of the model worker is detected, the work operation in the specific stage of the work procedure with respect to the three-dimensional shape included in the presented information is grasped as there-dimensional distance information, and the evaluation criterion information is created on the simulated work of the predetermined work procedure, based on the measurement information of the three-dimensional work operation. Therefore, by setting the body motion to be measured for the purpose of grasping the beginning and the duration of the important specific stage in the work procedure, a content creation system can be realized that can create a training content that can automatically and quantitatively grasp the work operation of the specific stage in which the know-how and the method for avoiding risk possessed by the expert worker and the like appear and contribute to the reduction of the man-hours for content creation by clarification of the important work operation, and effectively utilizable for determination of the training result by the evaluation criterion information.

The content creation system according to the present invention may be so configured that, the evaluation criterion creation device detects the predetermined body motion of the model worker as a variation in voice information or video information or a variation in three-dimensional measurement information.

By doing so, it is possible to timely and accurately acquire appropriate measurement information of the work operation which is important during the model work and to be noted from the line of sight, articulation, movement of fingertip and the like of the model worker such as an expert, to reliably reduce the man-hours required to specify the important work operation, and to enable the creation of effective evaluation criterion information.

The content creation system according to the present invention may be so configured that, the evaluation criterion creation device monitors a work operation in the specific stage as measurement information including a three-dimensional variation of a specific portion of interest of the model worker and time, when the predetermined body motion of the model worker is detected. Further, the content creation system according to the present invention may be so configured that, the content generation device updates the training content in the specific stage so as to be able to evaluate the work operation in the specific stage by the evaluation criterion information, when the predetermined body motion of the model worker is detected.

The content presentation system according to the present invention is a content presentation system that presents training content based on three-dimensional shape information of a work target device and a work procedure to a trainee, and has executed a simulated work in accordance with the work procedure in a simulated work space of virtual reality or augmented reality, the content presentation system comprising: a content output device that has a memory unit that stores the training content including the three-dimensional shape information and an output unit that outputs the training content to be presentable to the trainee; an evaluation criterion creation device that acquires a three-dimensional operation of the work of a model worker as measurement information during the simulated work, and creates evaluation criterion information on a work operation in a specific stage of the work procedure, based on distance information of a three-dimensional work operation with respect to the three-dimensional shape: and a work evaluation device that acquires three-dimensional work operation information in the simulated work of the trainee as measurement information, evaluates the three-dimensional work operation in the specific stage of the simulated work based on the evaluation criterion information, and outputs a result of the evaluation.

By this configuration, in the content presentation system according to the present invention, the work operation in the specific stage which is important in the work procedure is clarified as the three-dimensional operation information, the start time and the duration of the work operation can be grasped, and with regard to the work operation in the specific stage where the know-how and the method for avoiding risk possessed by the model worker and the like appear, the simulated work operation of the trainee can be quantitatively grasped and accurately determined by the evaluation criterion information, thereby making it possible to effectively utilize the training content for determination of the training results.

Effect of the Invention

By the present invention, it is possible to provide a content creation system capable of: easily and reliably reflecting an important work operation and evaluation criterion among model work by experts and the like to the training content for supporting the work: contributing to the reduction of man-hours for creation of the content; and creating content that can be effectively utilized for evaluating the training result.

BRIEF DESCRIPTION OF THE DRAWINGS

FIG. 6 is an explanatory diagram of a progress table content showing a progress status of a plurality of tasks managed by a work management server in a manual content presentation system according to one embodiment of the present invention.

FIG. 7 is an explanatory diagram of a progress table content exemplifying the content data materials including work procedures of the first task and collected information from experts at each stage on the work procedure from among a plurality of tasks shown in FIG. 6 and presented to the trainee FIG. 8 is an explanatory diagram of a measurement data sheet for collecting the content data materials shown in FIG. 7 from experts.

FIG. 12A is an explanatory diagram for the display screen at the time when the training content is distributed from the training management server to the training support terminal and the work operation and its determination process in the specific stage in the work procedure are executed, in a manual content presentation system according to one embodiment of the present invention, and FIG. 12A is an explanatory showing an example of the message display on the training support terminal FIG. 12A is an explanatory showing an example of the determination result display screen on the training support terminal.

DETAILED DESCRIPTION OF THE INVENTION

Hereinafter, embodiments for carrying out the present invention will be described with reference to the drawings.

FIGS. 1-8 show the configuration of a manual content presentation system including a content creation system according to one embodiment of the present invention and FIGS. 9-12 show a schematic procedure of content creation process in a manual content presentation system according to one embodiment of the present invention.

First, the configuration will be described.

Figure 1:
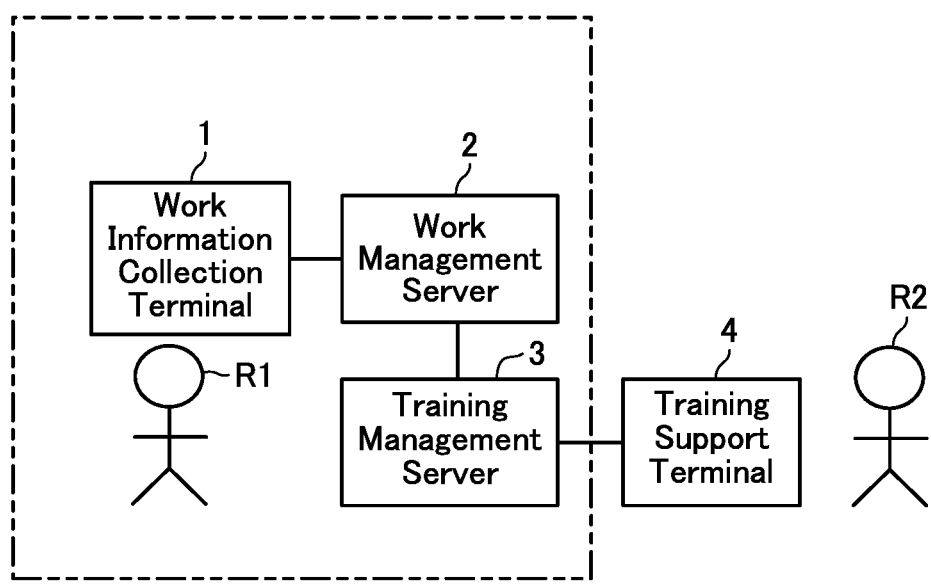
FIG. 1 is a schematic block configuration diagram showing the overall configuration of a manual content presentation system including a content creation system according to one embodiment of the present invention.

As shown in FIG. 1, the manual content presentation system including the content creation system according to the present embodiment has a work information collection terminal 1 arranged so that information can be inputted to the work site side, a work management server 2 for controlling a progress of the work in the work site side, a training management server 3 connected to the work management server 2 via a network and a training support terminal 4 capable of presenting training content from the training management server 3 to the trainee R2.

The work information collection terminal 1 is composed of, for example, an information terminal capable of presenting information to a worker who performs maintenance work on a predetermined system or device to be maintained and managed, for example, a head mount display which is a wearable terminal.

Figure 2:
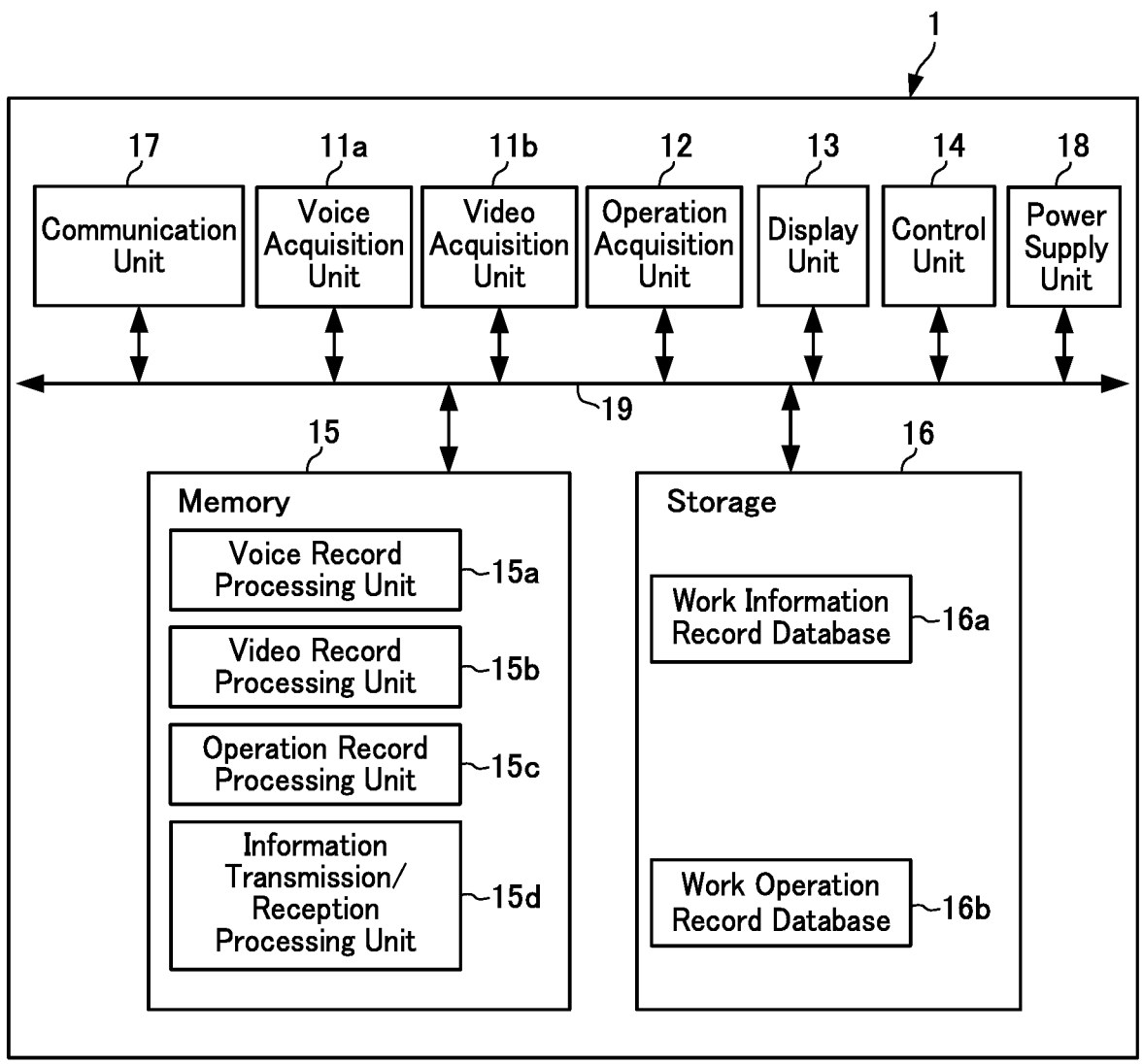
FIG. 2 is a schematic block configuration diagram of an information terminal on a worker side in a manual content presentation system according to one embodiment of the present invention.

As shown in FIG. 2, the work information collection terminal 1 includes a sound acquisition unit 11a and an image acquisition unit 11b capable of acquiring worker's physical information and work operation as sound information and image information, an operation acquisition unit 12 that acquires a work operation according to an operation procedure as three-dimensional information based on the acquired information of the image acquisition unit 11b, a display unit 13 capable of displaying a virtual 3D CG in a superimposed manner, for example, on a transmissive screen, and a control unit 14 of a microcomputer configured to be bus-connected with these information acquisition units 11a, 11b, and 12.

The work information collection terminal 1 is also provided with a memory 15 such as a RAM, a ROM, and a flash memory, or the like, a storage 16 such as an SSD (Solid State Drive) or the like, a communication unit 17 capable of local or wide area wireless communication, a power supply unit 18 that supplies power to each unit of the work information collection terminal 1, and a bus 19 that connects these units so that they can mutually communicate information.

The image acquisition unit 11b has a three-dimensional camera or a plurality of cameras capable of acquiring an image of the view area as 3D CG, and has a function of photographing and visualizing the site and the hand of the maintenance work so that the position can be measured. The display unit 13 may be of a non-transmissive type arranged in a part of the field of view. The communication unit 17 has a function of transmitting a signal of a video being displayed and a sound acquired by a microphone of the sound acquisition unit 11a to the outside by a predetermined transmission method.

The memory 15 has stored therein a plurality of control programs that stores the measurement information from the sound acquisition unit 11a and the image acquisition unit 11b that perform predetermined operation measurement processing as operation information, and a communication processing program that processes transmission/reception data by the communication unit 17. The memory 15 includes the voice recording processing unit 15a, the video recording processing unit 15b, the operation recording processing unit 15c, and the information transmission/reception processing unit 15d as functional units of the control programs.

The storage 16 has incorporated therein a storage control program that exercises the database function and includes a work information record database 16a for storing various kinds of work information input via the communication unit 17 by the function of the control program and a work activity record database 16b for recording the work information processed by each of the record processing units 15a to 15c in association with the work time.

Figure 3:
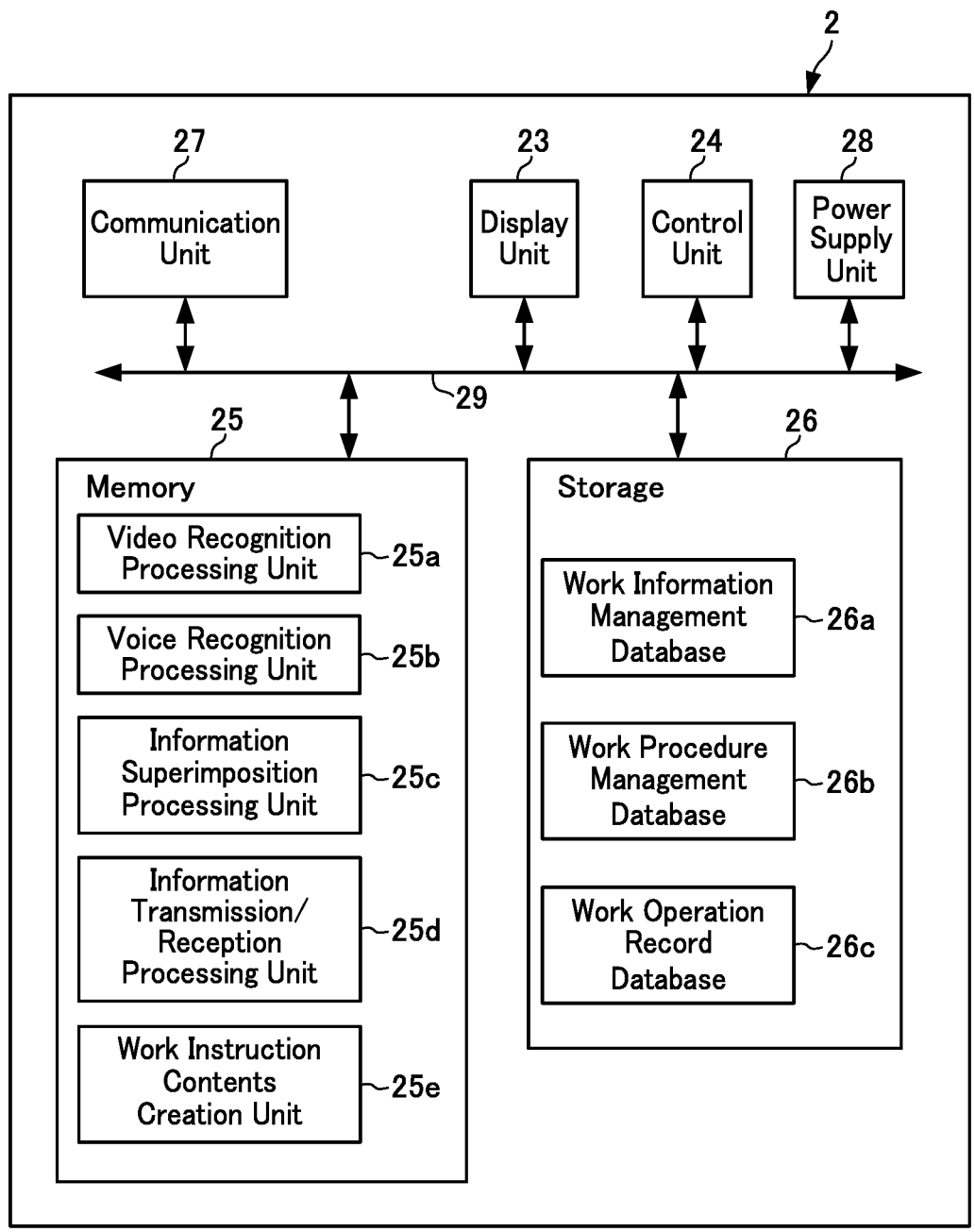
FIG. 3 is a schematic block configuration diagram of a work management server in a manual content presentation system according to one embodiment of the present invention.

As shown in FIG. 3, a work management server 2 includes a display unit 23 capable of displaying a maintenance work area from the work information collection terminal 1 and necessary support information in a superimposed manner, a control unit 24 controlling the entire server, a memory 25, a storage 26, a communication unit 27 capable of local or wide area wireless communication, a power supply unit 28 for supplying power to each unit of the work management server 2, and a bus 29.

A plurality of control programs is stored in the memory 25, and the storage 26 has incorporated therein a storage control program. The control unit 24 recognizes a maintenance work area corresponding to the view area as 3D CG and voice information in cooperation with the sound acquisition unit 11a, the image acquisition unit 11b, and the memory 15 of the work information collection terminal 1, and as described above, functions as an operation measurement device that acquires the three-dimensional work operation of a model worker R1 who is an expert or the like performing a work of a predetermined procedure.

Specifically, the control programs stored in the memory 25 and the storage 26 have the memory 25 function in cooperation with the control unit 24 as a plurality of functional units which include an image recognition processing unit 25a and a voice recognition processing unit 25b capable of recognizing the maintenance work area and worker's physical information and work operation acquired from the work information collection terminal 1, respectively as the 3D CG information and voice information. The functional units further include an information superimposition processing unit 25c that displays a marker information and other support information in a superimposing manner on the view area acquired by the image acquisition unit 11b and recognized by the image recognition processing unit 25a, an information transmission/reception processing unit 25d that receives the image acquired by the image acquisition unit 11b from the work information collection terminal 1 and transmits the support information necessary to be displayed in a superimposition manner on the view area of the work information collection terminal 1 to the work information collection terminal 1, and a work instruction content creation processing unit 25e that creates a work instruction content to be transmitted to the work information collection terminal 1.

In addition, the storage 26 includes a work information management database 26a for managing the three-dimensional shape information of the operation target devices and various work information for creating training content based on the work procedure, a work procedure management database 26b for managing the work procedure corresponding to the work instruction content created by the work instruction content creation processing unit 25e as a part of the manual content, and a work operation record database 26c for recording worker's physical information and the three-dimensional information of each work operation and the like recognized by the image recognition processing unit 25a and the voice recognition processing unit 25b together with time information.

In the work information management database 26a of the storage 26, at least, for example, information on the worker who performs maintenance and inspection work, identification information on device for performing maintenance and inspection work, maintenance schedule information including execution date and time of maintenance inspection work, maintenance and inspection information indicating the content of the maintenance and inspection work and the like are recorded.

The control unit 24 of the work management server 2 is capable of determining whether or not each stage of the work procedure is a specific stage that needs evaluation determination based on the 3D CG and voice and the like of the maintenance work area and the 3D CG and the voice and the like of the worker's physical information and the wok operation against the maintenance target device recognized by the image recognition processing unit 25a and the voice recognition processing unit 25b The control unit 24 is also capable of measuring the three-dimensional work operation in the specific stage, as a relative movement against the work target (a fixed work target or a work target on a support side that movably supports a movable work target) and a work time accompanying the movement, based on the movement of the worker's line of sight and arms (which may be part of other bodies such as the neck, hands, fingers, feet, etc.), the movement of the feature points wearing the markers.

The control unit 24 of the work management server 2 also detects a predetermined body motion of the model worker R1 such as an expert worker as at least one of line of sight, voice, and three-dimensional motion via the work information collection terminal 1. In addition, the control unit 24 detects the work operation in the specific stage in the predetermined work procedure, as a variation in the voice information or visual field image information or a variation in three-dimensional measurement information preceding or following the predetermined operation, for example, following the predetermined operation. Then, the control unit 24 creates an evaluation criterion of the work operation in the specific stage described above, based on the measurement information of the three-dimensional work operation through the work information collection terminal 1.

The predetermined body motion referred to herein includes, for example, a body motion of an expert who performs model work that the expert produces words and voices such as "Everybody must be careful here." or "This is an important work." and the like, a gesture such as pointing a finger accompanying the words and voices, or a motion serving as a signal for entering a specific stage. This predetermined body motion may include a motion which serves as a signal for ending the specific stage at the time when the operation motion in the specific stage of the work procedure comes to an end. The work time of the work operation in the specific stage is preset as the work time required for the corresponding work operation of the model work at the stage.

The evaluation criterion is so set that the evaluation is higher as, for example, the position of the viewpoint, the motion position of the arm and the position of the marker serving as a feature point and the like are closer to those in the work operation of the model worker R1 such as the expert worker and the like, with regard to the work operation against the work target devices in the simulated work space of the virtual reality or the augmented reality which is the work of the training.

For example, this evaluation criterion is set by comparing the work operation position for each equally divided time during the required time of the work operation in the specific stage for the model worker R1 and the trainee R2, by comparing the length of the required time of the work operation in the specific stage, by weighting the measured value corresponding to the difference between the working operation positions of both of them, or by furthermore comparing other body movements that can be detected by the motion sensor or the biometric sensor during the required time of the task operation in the specific stage.

The work instruction content creation processing unit 25e is adapted to create a work instruction content including the aforementioned evaluation criterion of the work operation in the specific stage, by adding the model work, its know-how, notes and the like to the items described in the manual, based on the work-related information, the work procedure information, and the work operation record information stored in the storage 26.

The work management server 2 of the present embodiment, configured as described above, functions as an evaluation criterion creation device referred to in the present invention, and is capable of monitoring the work operation in the specific stage as measurement information including three-dimensional displacement and time for the displacement of a specific attention site of the model worker, at the time when a predetermined body motion of the model worker R1 is detected.

The work instruction content created by the work instruction content creation processing unit 25e of the work management server 2 is transmitted to the training management server 3 via the information transmission/reception processing unit 25d.

Figure 4:
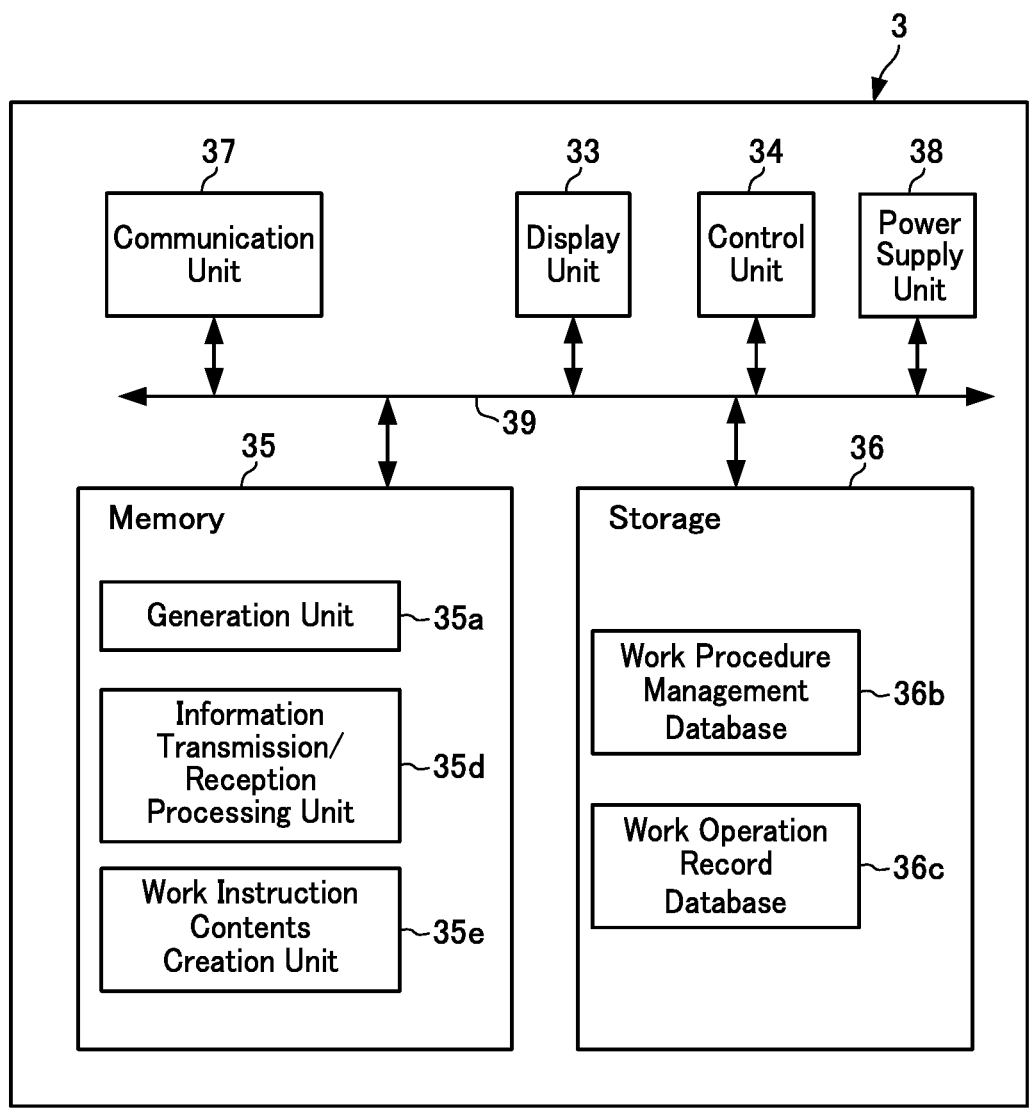
FIG. 4 is a schematic block configuration diagram of a training management server in a manual content presentation system according to one embodiment of the present invention.
Figure 5:
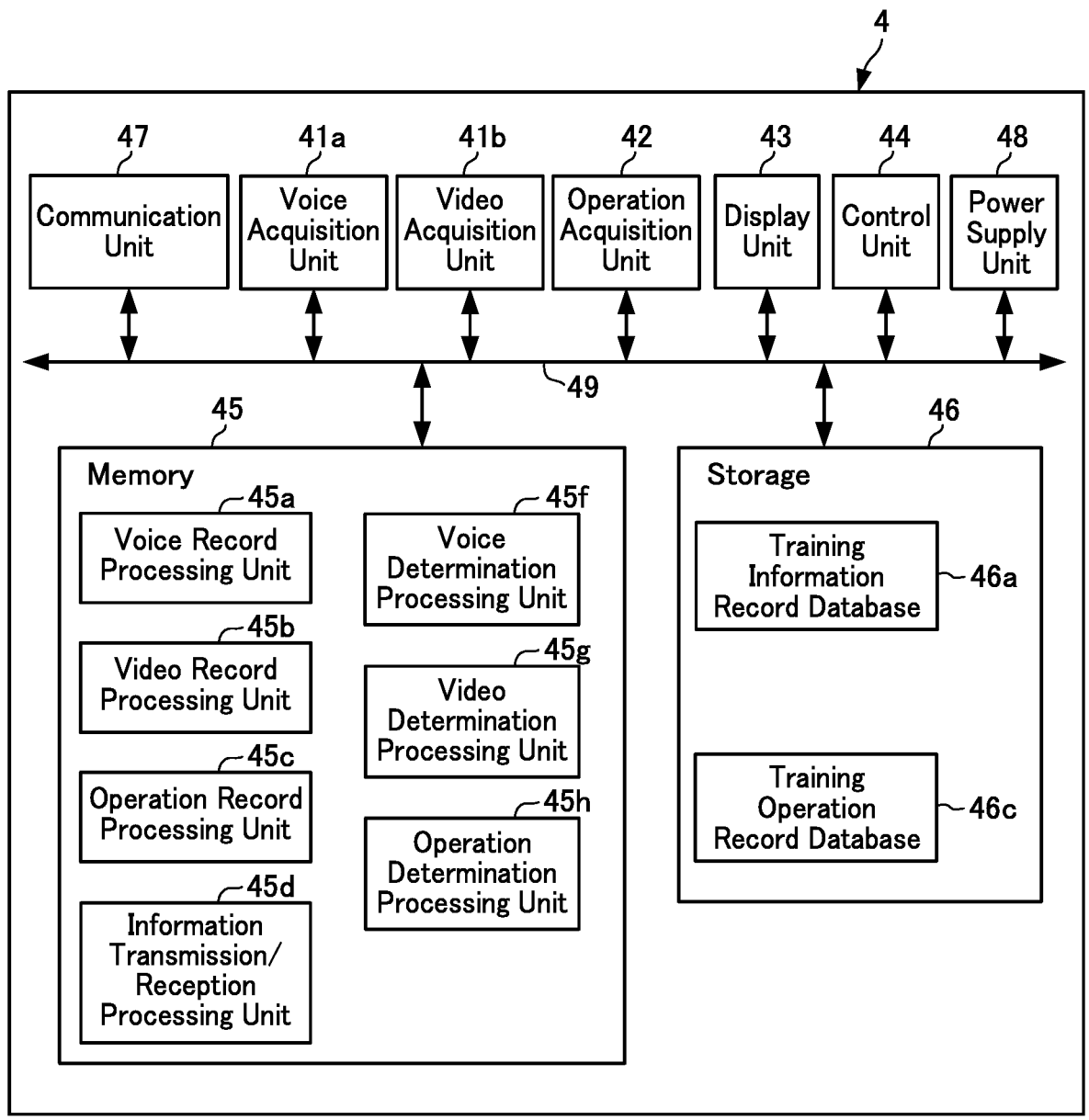
FIG. 5 is a schematic block configuration diagram of an information terminal on a trainee side in a manual content presentation system according to one embodiment of the present invention.

As shown in FIGS. 4 and 5, the training management server 3 includes a display unit 33 capable of displaying work instruction content from the work management server 2 on a screen, a control unit 34 that controls training management, a memory 35, a storage 36, a communication unit 37 capable of local or wide area wireless communication, a power supply unit 38 that supplies power to each unit of the work management server 2, and a bus 39 that connects these units so that they can mutually communicate information.

In addition, the training support terminal 4 includes a voice acquisition unit 41a and an image acquisition unit 41b capable of acquiring physical information and work operation of the trainer as sound information and image information, an operation acquisition unit 42 for acquiring a corresponding work operation as three-dimensional information based on acquired information of the image acquisition unit 41b, a display unit 43 capable of, for example, superimposing and displaying a virtual 3D CG on a transmissive screen, and a control unit 44 of a microcomputer configuration connected to these information acquisition units 41a, 41b, 42 via a bus.

The image acquisition unit 41b of the training support terminal 4 has a three-dimensional camera or a plurality of cameras capable of acquiring an image of the view area as 3D CG and has functions to photograph and visualize the site and hand of the maintenance work area in a position measurable manner. The display unit 43 may be of a non-transmissive type arranged in a part of the field of view.

Furthermore, the training support terminal 4 includes a memory 45 such as a RAM, a ROM and a flash memory, a storage 46 such as an SSD, a communication unit 47 capable of local or wide area wireless communication, and a power supply unit 48 that supplies power to each unit of the training support terminal 4, and a bus 49 that connects these units so that they can mutually communicate information. The communication unit 47 has functions to externally transmit the signal of the image being displayed and the sound acquired by the microphone of the sound acquisition unit 41a by a predetermined transmission method.

In the training management server 3 shown in FIG. 4, a plurality of control programs is stored in the memory 35, and the storage 36 has incorporated therein a storage control program. The training management server 3, by function of the control programs cooperating with the control unit 34, recognizes the maintenance work area corresponding to the view area of the training support terminal 4 as 3D CG and sound information, and superimposes and displays the work support information on the work area in the recognized view area or a part thereof on the display unit 33, based on the work instruction content from the work management server 2.

In addition, by function of the control programs cooperating with the control unit 34, the training management server 3 displays the position of the viewpoint, the movement position of the arm, the position of the feature point and the like by their respective markers each showing a target position which is a three-dimensional work operation position of the model worker, and also displays, for example, the next target point for each equal division time described above, when the attention point position of the corresponding work operation of the trainee R2 approaches within the fixed distance range of the respective target position. Then, the training management server 3 evaluates an operation speed of the immediately preceding work operation by detecting the difference in speed between the work operation and that of the corresponding model worker, and evaluates the operation speed based on the evaluation criterion. In other words, a judgment processing is performed in which the evaluation value becomes higher as the temporal and spatial deviation from the evaluation criterion for each predetermined work operation is smaller. Such evaluation may be conducted based only on the length of the operation time in the specific stage depending on the content of the work in the specific stage such as the content of the maintenance work.

To be more specific, the control programs stored in the memory 35 and the storage 36 of the training management server 3 serves as a plurality of functional units constituted by the control programs cooperating with the control unit 34 and including a generation unit 35a that generates manual content that reflect the content of work instruction content from the work management server 2, such as the working time and the like of the work operation in the specific stage in the model work, additionally to the existing training manual content of a predetermined work procedure including, for example, device identification information, maintenance schedule information and maintenance inspection information and the like of the work target The memory 35, serving as a functional unit by the control programs cooperating with the control unit 34, also has an information transmitting/receiving processing unit 35d that transmits manual content to the training support terminal 4 and receives information such as 3D CG and the voice of the work operation acquired by the training support terminal 4 and a work instruction content creation processing unit 35e that updates or corrects the content to be used in the generation unit 35a, based on the update information of the work instruction content from the work management server 2 or the feedback information such as the determination processing result or the like from the training support terminal 4.

In addition, the storage 36, serving as a functional unit by the built-in storage control program cooperating with the control unit 34, has a work procedure management database 36b that manages, for example, the work procedure corresponding to the work instruction content created, updated or corrected by the work instruction content creation processing unit 35e and a work operation record database 36c that records the physical information recognized by the training support terminal 4 and the three-dimensional information of each work operation together with the time information.

The training management server 3 of the present embodiment configured as described above functions as a content creation device according to the present invention, and is capable of updating the training content so that the work operation of the specific stage of the training content can be evaluated based on the evaluation criterion information, when a predetermined body motion of the model worker R1 is detected.

The training support terminal 4, as a man-machine interface for storing the measurement information under training as operation information and for determining the degree of proficiency of a specific work operation under training based on the aforementioned evaluation criterion, has a plurality of input/output devices for videos and voices and a plurality of control programs provided therein. By function of those input/output devices and control programs, as shown in FIG. 5, the training support terminal 4 includes a voice recording processing unit 45a, an image recording processing unit 45b, an operation recording processing unit 45c, an information transmission/reception processing unit 45d, a voice property determination processing unit 45f, a video determination processing unit 45g, and an operation determination processing unit 45h.

The voice acquisition unit 41a and the video acquisition unit 41b of the training support terminal 4 have functions of acquiring the body motion and the work operation during the training work of the trainee as a sound and a three-dimensional image, and measure, for example, trainee's line of sight, motion of arms and motion of the feature points.

The operation record processing unit 45c specifies the work operation in each stage from the video and voice information acquired by the voice acquisition unit 41a and the video acquisition unit 41b according to the work procedure prescribed by the manual content.

The information transmission/reception processing unit 45d transmits the information acquired by the voice acquisition unit 41a, the image acquisition unit 41b, and the operation record processing unit 45c to the training management server 3, and receives the manual content and its update information from the training management server 3.

The voice determination processing unit 45f, the image determination processing unit 45g, and the motion determination processing unit 45h are configured to specify work operation in each stage of the work procedure prescribed by the manual content, in light of the evaluation criterion for the work operation in the specific stage, based on information such as video and voice recorded and processed by the recording processing units 45a to 45c of the memory 45, and have functions to determine and evaluate the work operation in the specific stage associated with the work time. The method of evaluating the work operation is as described above.

In the storage 46, a control program for exercising the database function is built in, and by function of the control program, the storage 46 includes a training information record database 46a that stores various kinds of information related to the training of the trainee input via the communication unit 47, and a training operation record database 46c for recording the determination results at the respective record processing units 45a 45c and the respective determination units 45f-45h of the memory 45 in association with the working time.

Next, the content of information presentation based on more specific manual content will be explained with reference to the progressive table content, the procedure table content, and the measurement data sheet of the content data material included in the manual content of the plurality of tasks as shown in FIGS. 6 to 8.

In the progress table content shown in FIG. 6, the planned execution dates, the start/end times of the plurality of operations, the corresponding task names and the results thereof are shown together with the index numbers indicating an order of the work execution. For example, the first task among the work is the completed task "Air Conditioner, Electric Circuit Exchange" of the index 1, the next task is the ongoing task "Air Conditioner, Substrate Exchange" in the index 2. The task of index 3 is not yet implemented "Air Conditioner Centralized Controller, Wiring Inspection".

The procedural table content shown in FIG. 7 exemplifies the procedure corresponding to the first task of the progress table content shown in FIG. 6. In FIG. 7, the index in each stage of the work procedure is indicated by a number, the task name of the task constituted by the multi-step work operation is displayed, and the work operation of each stage is shown as a procedure together with the corresponding content data material.

In this procedural table content, with respect to the work name "Air Conditioner, Electric Circuit Exchange" shown in FIG. 7, the work operations constituted by a plurality of stages are performed from the work operation "Check the object" of index 1 to the work operation "Open Cover" of index 2, the work operation "Remove Circuit" of index 3, the work operation "Attach Circuit" of index 4 and the work operation "Attach Cover" of index 5 in this order, and finishes with the work operation "Confirm No Problem in Operation." of index 6.

Based on this progress table content, the training support terminal 4 displays a photograph (item.jpg) or 3D CG (item.fbx) for specifying the work target area and the work target and an explanation about notes and the like on current operation (manual_1.txt), during the work operation of the index 1.

Also, during work operation of the index 2, in order to open the cover, a photograph (Cover.jpg) or 3D CG (Cover.fbx) of the cover is displayed, and a video with voice for explaining the content of the current work operation (instruction_2.mp4) is played back and an explanatory display (manual_2.txt) is made. During the work operation of the index 3, in order to remove the electric circuit before replacement, a photograph (electronic_circuit.jpg) of the electric circuit board and the like and the 3D CG (electronic_circuit.fbx) around the attachment position is displayed, the video with voice (instruction_3.mp4) explaining the content of the current work operation is played back, and the explanation display (manual_3.txt) is displayed.

During the work operation of the next index 4, in order to attach the new electric circuit to the replacement target portion, a photograph (electronic_circuit.jpg) of the electric circuit board or the like and 3D CG (electronic_circuit.fbx) around the attachment position are displayed. Further, the video with voice (instruction_4.mp4) explaining the current working operation content is played back and the explanation display (manual_4.txt) is displayed.

During the work operation of the next index 5, in order to attach the cover, a photograph of the cover (Cover.jpg) or 3D CG (Cover.fbx) is displayed, and at the same time, the video with voice (instruction_5.mp4) explaining the current working operation content is played back, and the explanation display (manual_5.txt) is displayed. And during the work operation at the last index 6, in order to confirm that there is no problem in the work operation in each stage of the series of work procedures, a photograph (Item.jpg) and 3D CG (item.fbx) for specifying the work target area and work target and the explanatory indication (manual_6.txt) on the current work operation notes and the like are displayed.

On the other hand, in the present embodiment, when preparing manual content for training accompanied by information presentation as exemplified above, before the creation of the manual content including the work procedure or during the creation thereof, an expert worker wearing the work information collection terminal 1 performs a model work in a predetermined work procedure, at least the work operation in the specific stage at which expert know-how and caution must be exerted by the expert are specified, and the information on the work operation of the model work that constitutes the evaluation criterion for the work operation in the specific stage is acquired.

FIG. 8 shows a measurement data sheet of the content data material when collecting information on such model work.

In this measurement data sheet, the work operations of model work by experts are sequentially executed according to the work procedure conforming to the content of manual description, and work operations in each stage are collected in association with each measurement start or end time information along with the index number and the implementation date, as measurement data including a line of sight variation based on a fixed object in the work target area, a variation in movement of the arm and a variation in remarkable feature point and voice variation.

Here, for the line of sight measurement, for example, a viewpoint monitoring technique using an eye camera (for example, refer Re-publication of PCT International Publication No. 2016/002056) can be used, and in measuring the variation amount of the movement of the line of sight and the arm, for example, a mapping technique of a difference in measurement values onto a three-dimensional space (for example, refer Japanese Patent Application Laid-Open No. 2018-10630) can be used.

The variation in the line of sight (start_eye.csv in FIG. 8) may include, for example, an angle variation in the line of sight direction with respect to the visual field image center direction of the work information collection terminal 1. The variation in the line of sight is measured with respect to the work operation position at the start of work in the work period in each stage or with respect to the work operation position at the start of work and the aforementioned equally divided time. Further, the feature point variation (start_featurepoint.csv in the figure) and the arm motion variation (start_arm.csv in FIG. 8) can be measured by various known motion analysis methods (for example, refer Re-publication of PCT International Publication No. 2015/189994).

Thus, the content creation system according to the present embodiment, which performs three-dimensional work operation measurement, has the work management server 2 functioning as an evaluation criterion creation device that creates the evaluation criterion information on the work of the work procedure based on the measurement information of the three-dimensional work operation through the work information collection terminal 1 and the training management server 3 functioning as a content creation device that creates and updates the training content based on measurement information of three-dimensional work operation, evaluation criterion information, and three-dimensional shape information of work target devices. The work management server 2, serving as an evaluation criterion creation device, creates training content based on the distance information on the three-dimensional work operation position in a specific stage with respect to the three-dimensional shape of the work target, on the condition that at least either one of the predetermined line of sight variation, the voice variation and the three-dimensional work operation which is the predetermined body motion of the model worker R1 is detected. The work management server 2 is capable of reflecting important work operation and evaluation criterion of the model work of the model worker R1 such as experts on the training content that can support the work, prior to presenting the training content to the trainee R2 by the content presentation system.

The content presentation system of the present embodiment using the training content created by the content creation system according to the present embodiment presents the trainee R2 with the three-dimensional shape information of the work target device and the training content based on the work procedure, has a simulated work executed in accordance with to the work procedure in a simulated work space of virtual reality or augmented reality, and includes: a training support terminal 4 that has the storage 46 that stores training content including three-dimensional shape information and a display unit 43 that outputs the training content so that it can be presented to the trainee R2; the work management server 2 that acquires, as a measurement information, the three-dimensional movement of the work of the model worker R1 that preliminarily executes work conforming to the work procedure and creates the evaluation criterion information on the work operation in the specific stage out of the series of work based on the distance information of the three-dimensional work operation on the three-dimensional shape of the work target: the control unit 44 serving as the work evaluation device that acquires the three-dimensional work operation during the simulated work for training of the trainee R2 as measurement information, evaluates the three-dimensional work operation in the specific stage during the simulated work based on the evaluation criterion information, and outputs the result of the evaluation; and the memory 45.

Next, the operation will be described.

Figure 9:
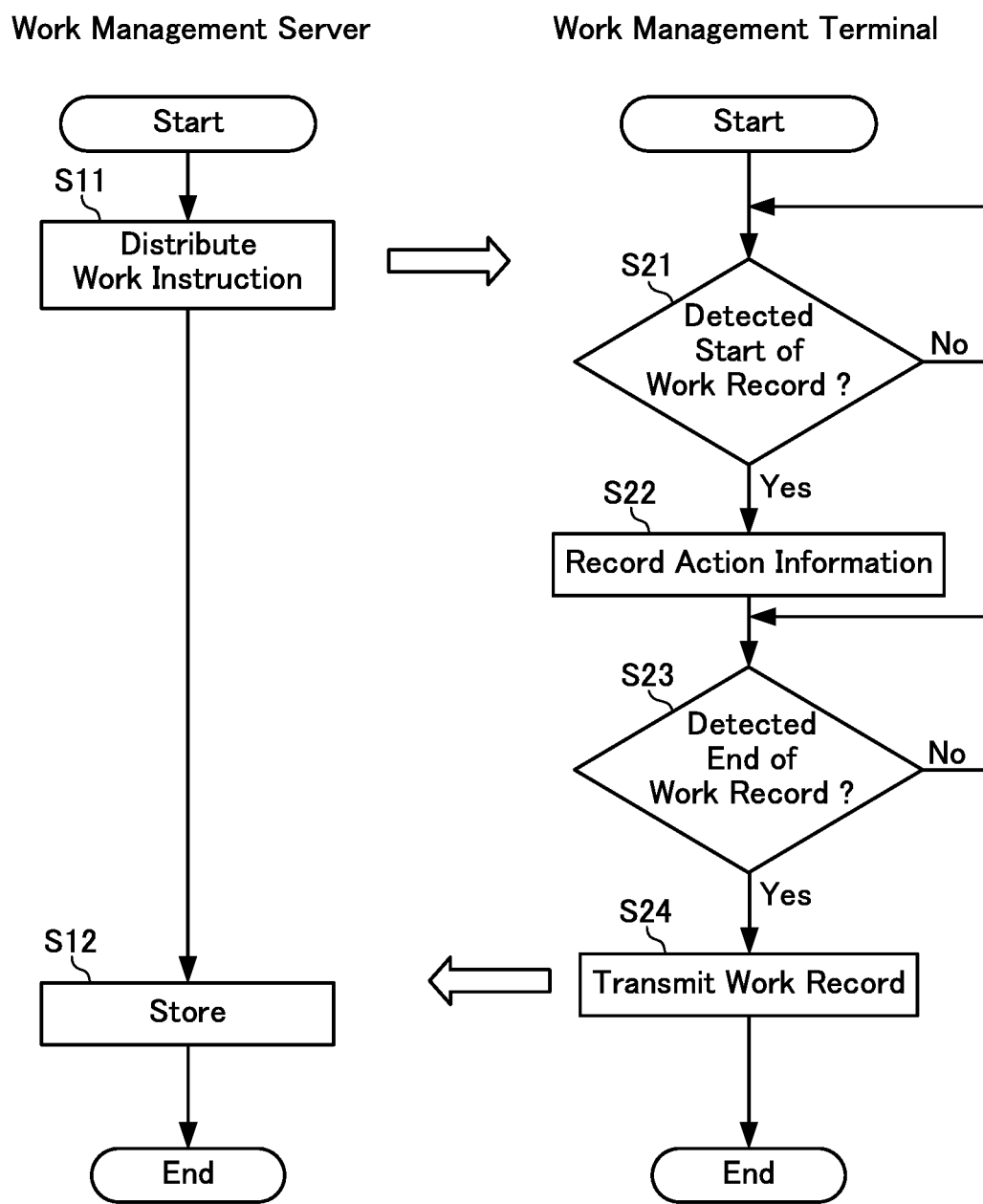
FIG. 9 is a sequence chart showing a procedure for having the expert worker execute the work operation in the specific stage accompanied by a predetermined body motion in accordance with the work procedure following the work instruction from the work management server and recording the work operation in a manual content presentation system according to one embodiment of the present invention

In the work presentation system including the content creation system of the present embodiment, as shown in FIG. 9, a work instruction for collecting information on the model work is issued from the work management server 2 to the work information collection terminal 1 (step S11), and if the start of the work record is detected on the side of the work information collection terminal 1 (Yes in step S21), the activity information of the worker according to the work procedure is recorded in the storage 16 of the work information collection terminal 1 (step S22).

Subsequently, when it is detected by operation analysis, switch operation input, voice input or the like that the recording of the work operation in each stage has been completed from the time when the start of the work record is detected (Yes in step S23), information of the work record is transmitted from the work information collection terminal 1 to the work management server 2 (step S24) and stored as a work operation record in the storage 26 of the work management server 2 (step S12).

Figure 10:
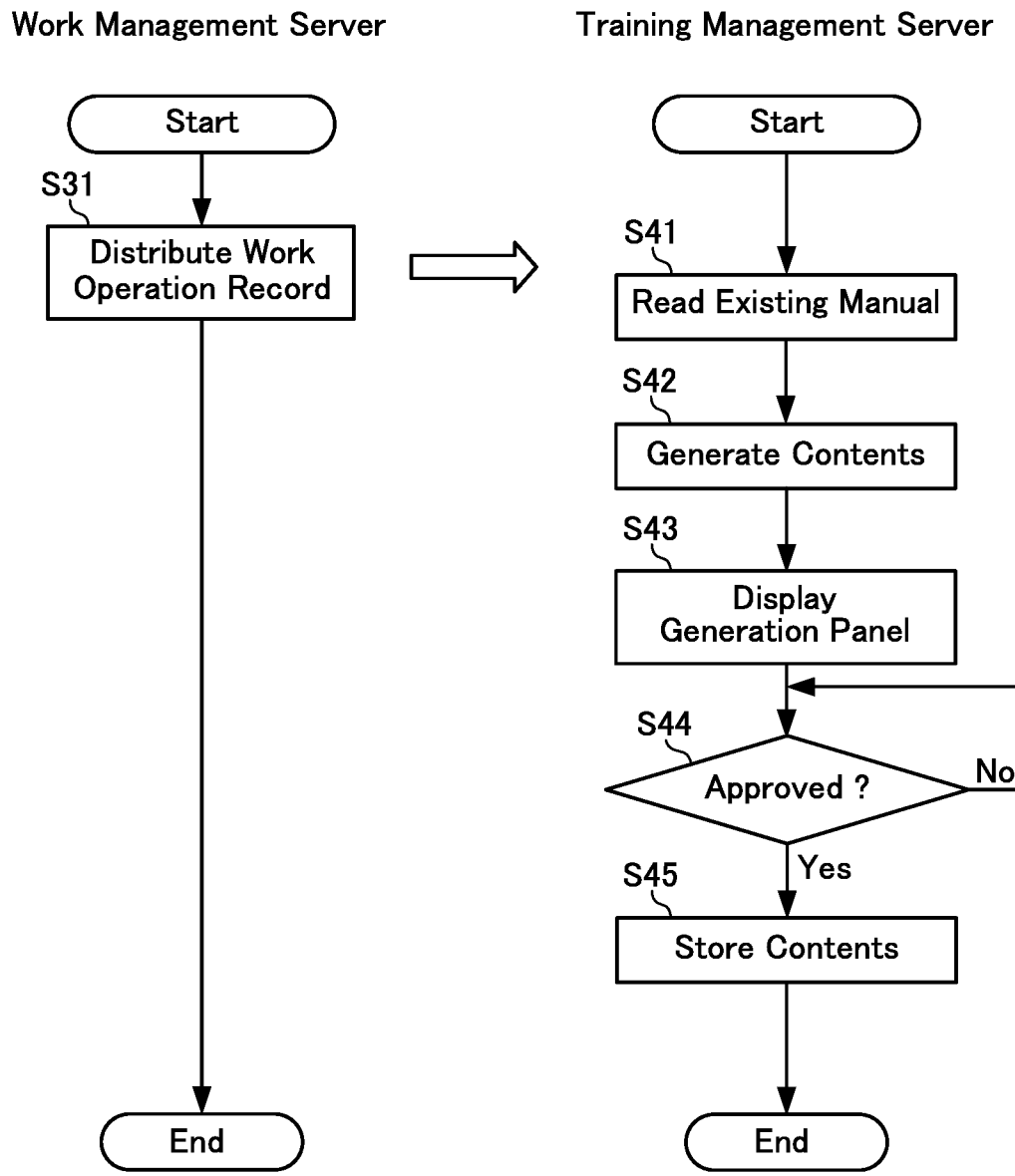
FIG. 10 is a sequence chart showing a process of distributing a work operation record from a work management server to a training management server, and generating, confirming and storing a material for training content based on the distribution information, in a manual content presentation system according to one embodiment of the present invention.

As shown in FIG. 10, when the work operation record is distributed from the work management server 2 to the training management server 3 (step S31), the existing manual recorded in the storage 36 of the training management server 3 is read (Step S41) and the manual content, reflected with the content of the work instruction content from the work management server 2 to the items of the existing training manual content, in other words, including the aforementioned evaluation criterion of the work operation in the specific stage in addition to the model work, its know-how, notes and the like, is generated by the generation unit 35a of the training management server 3 (step S42).

Next, the generated manual content is displayed on the display unit 33 of the training management server 3 or further on the display unit 23 of the work management server 2 (step S43), and if the changes are approved by the administrator who is the user (Yes in step S44), the generated manual content is stored in the storage 36 (step S45).

Figure 11:
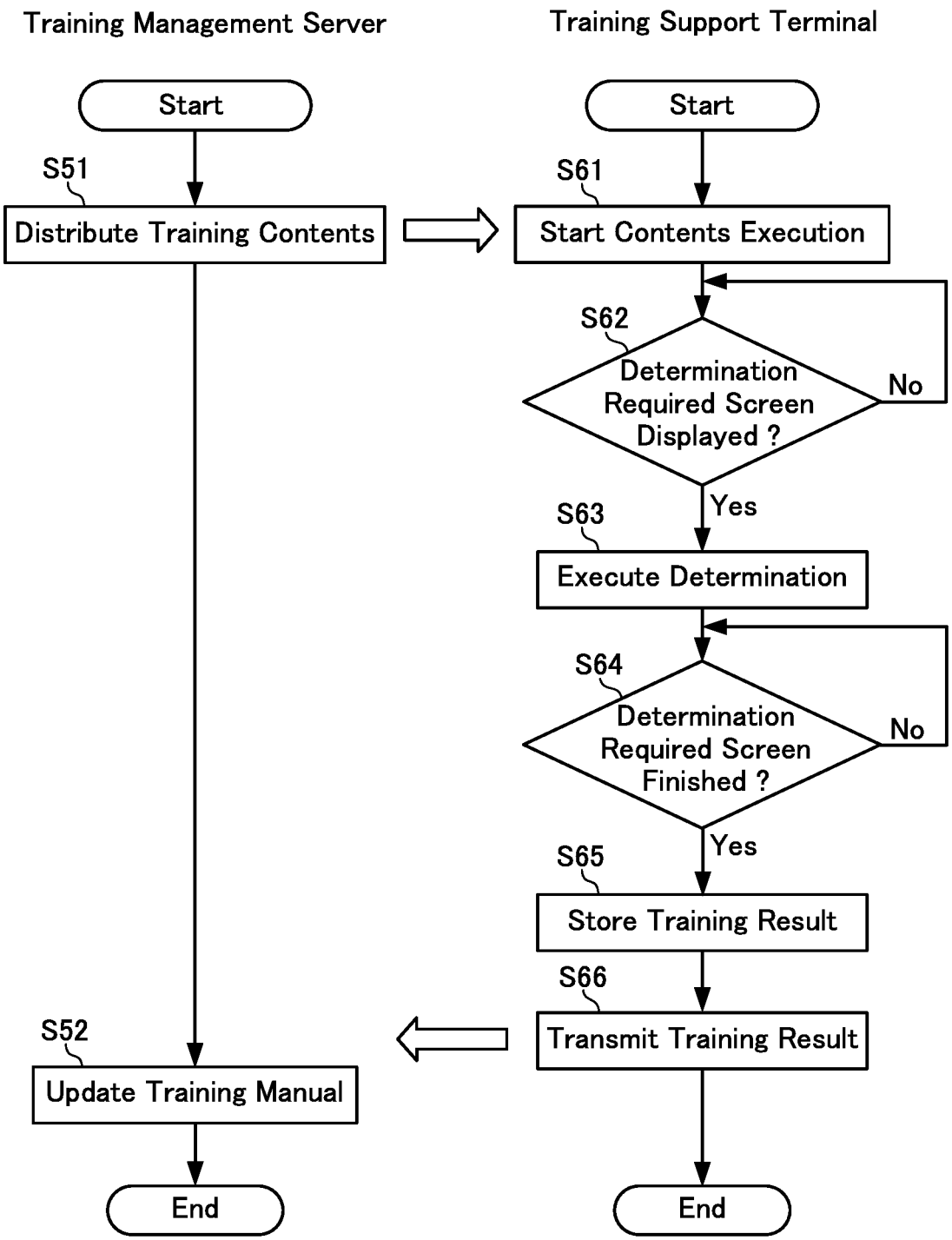
FIG. 11 is a sequence chart showing a process of distributing training content from a training management server to a training support terminal, executing a work operation in each stage in accordance with work procedures, executing a determination process of the training result about the work operation in the specific stage, and selectively executing an update process of the training manual with the training result, in a manual content presentation system according to one embodiment of the present invention.

As shown in FIG. 11, when the training content is distributed from the training management server 3 to the training support terminal 4 (step S51), the training support terminal 4 starts execution of the training content (step S61), and the work operation in each stage in accordance with the work procedure is presented to the trainee in a manner that is perceivable together with the support information.

Next, when the training support screen for executing the work operation in the specific stage in the work procedure is displayed (Yes in step S62), the determination process based on the evaluation criterion for the work operation in the specific stage is executed (step S63).

Then, when the training support screen for executing the work operation in the specific stage in the work procedure is finished (Yes in step S64), the training result is stored (step S65), and the training result is transmitted from the training support terminal 4 to the training management server 3 (step S66).

Then, in accordance with the content of the training result, the training management server 3 updates at least the training record information so as to include the training result information, and furthermore, considering the predetermined number or more of training results and update information from the outside, necessary update process is executed (step S52).

Figure 12B:
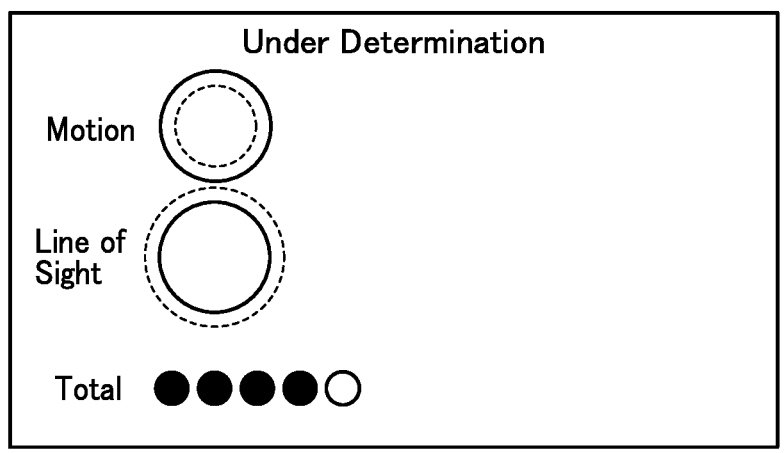
FIG. 12B is an explanatory diagram for the display screen at the time when the training content is distributed from the training management server to the training support terminal and the work operation and its determination process in the specific stage in the work procedure are executed, in a manual content presentation system according to one embodiment of the present invention.

When the aforementioned training is executed, as exemplified in FIG. 12A, massage display and voice output for start "Training starts, Please install necessary sensors" are preliminarily made, and when the training result is transmitted from the training support terminal 4 to the training management server 3, as exemplified in FIG. 12B, the determination result display screen on the movement of the arm, the movement of the line of sight and the like is displayed in the training support terminal 4.

As described above, in the present embodiment, when a predetermined body motion of the model worker R1, for example, a voice "This is an important work." is detected, the work operation in the specific stage is grasped in association with the work time as its three-dimensional distance information, so that the evaluation criterion information for the work of the predetermined work procedure of the trainee R2 based on the measurement information of the three-dimensional work operation is created based on the distance information.

Therefore, by setting the body motion to be measured for the purpose of grasping the start timing and the duration of the specific stage that is important in the work procedure, as, for example, voice emanating a specific word, movement of hand, variation of line of sight, movement of neck and the like, it is possible to automatically and quantitatively grasp the work operation in the specific stage where the know-how and the method for avoiding risk possessed by model workers and the like appear, thereby realizing a content creation system capable of creating a training content that can contribute to the reduction of man-hours for content creation through clarification of important work operations, and in addition, effectively utilizable for determination of training results through the evaluation criterion information.

Further, in the present embodiment, the work management server 2 serving as the evaluation criterion creation device detects a predetermined body motion of the model worker as a variation in voice information or video information or a variation in three-dimensional measurement information. Therefore, it is possible to acquire accurate measurement information of an important or cautious work operation during model work from time to time, remarks of the model worker R1 such as experts or remarks of the expert, timely and accurate movements of the hand, and the like, thereby making it possible to reliably reduce the man-hours required for specifying the evaluation criterion information, and to enable the creation of the evaluation criterion information.

As described above, in the present embodiment, it is possible to easily and reliably reflect the important work operation and evaluation criterion of the model work by experts and the like in the training content, contributing to the reduction of the content creation man-hours, thereby making it possible to provide a content creation system capable of creating content that can be effectively utilized for determination of the training result.

Further, in the content presentation system of the present embodiment using the training content created by this content creation system, the work operation in the specific stage which is important in the work procedure is clarified as the three-dimensional operation information, the start time and the duration of the work operation can be grasped, and with regard to the work operation in the specific stage where the know-how and the method for avoiding risk possessed by the model worker R1 and the like appear, the simulated work operation of the trainee R2 can be quantitatively grasped and accurately determined by the evaluation criterion information, thereby making it possible to effectively utilize the training content for determination of the training results.

It should be noted that in the operation management server 2 of the present embodiment, the existing manual content are preliminarily recorded and the specific work operation of the model worker who is an expert of the site work is recorded as the variation of the voice, operation and the line of sight immediately after the detection of the specific body motion. However, the operation management server 2 may otherwise be so configured that the training manual or the pre-training manual can be created based on the record information from the work operation collection server 1 inputted in each of the stages, from the state without existing manual content.

It goes without saying that, as in the above-described embodiment, when a predetermined body motion of the model worker is detected, the content generating device can update the existing training content so that the work operation in the specific stage in the work procedure can be evaluated by the evaluation criterion.

Further, at the time of executing the manual content, the training support terminal 4 compares the work operations of the trainee and the model worker only with respect to the work operation in the specific stage, and determines the work ability by training result. However, it goes without saying that the training support terminal 4 is capable of making a pass/fail determination based on the evaluation criterion for the work operation in the specific stage and determining the result of the whole training by the simulated work.

Even by doing so, it is possible to create and update a training manual based on the work of the expert as criterion for determining the proficiency degree of work, thereby making it possible to reduce the manual creation cost and clarify the undocumented know-how.

As described above, the present invention can provide a content creation system capable of easily and reliably reflecting important work operations and evaluation criterion of the model work to the training content, and contributing to reduction of content creation man-hours, and in addition, creating content that can be effectively utilized for determining the training result. The present invention as described above is generally useful for a content creation system for creating training content including 3D CG for executing a simulated work.

EXPLANATION OF REFERENCE NUMERALS

1 Work Information Collection Terminal (Operation Measurement Device, Site Work Support Terminal)
2 Work Management Server (Evaluation Criterion Creation Device)
3 Training Management Server (Content Creation Device)
4 Training Support Terminal (Content Output Device)
11a, 41a Voice Acquisition Unit
11b, 41b Image Acquisition Unit
12, 42 Operation Acquisition Unit
13, 23, 33 Display Unit
14, 24, 34 Control Unit
15, 25, 35 Memory
15a, 45a Voice Recording Processing Unit
15b, 45b Image Recording Processing Unit
15c, 45c Operation Record Processing Unit
15d, 45d Information Transmission/Reception Processing Unit
16, 26, 36 Storage
16a Work Information Record Database
16b Work Operation Record Database
17, 27, 37, 47 Communication Unit
18, 28, 38, 48 Power Supply Unit
19, 29, 39, 49 Bus
25a Image Recognition Processing Unit
25b Voice Recognition Processing Unit
25c Information Superimposition Processing Unit
25d, 35d Information Transmission/Reception Processing Unit 25e, 35e Work Instruction Content Creation Processing Unit
26a Work Information Management Database
26b, 36b Work Procedure Management Database
26c, 36c Work Operation Record Database
35a Generation Unit
43 Display Unit (Output Unit)
44 Control Unit (Work Evaluation Device)
45 Memory (Operation Evaluation Device)
45f Voice Determination Processing Unit
45g Image Determination Processing Unit
45h Operation Determination Processing Unit
46 Storage (Storage Unit)
46 a Training Information Record Database
46 c Training Operation Record Database
R1 Model Worker (Expert)
R2 Trainee

The invention claimed is:

1. A content creation system that creates training content to be presented to a trainee based on a three-dimensional shape of a work target device and a work procedure to have executed a simulated work of virtual reality or augmented reality, the content creation system comprising:
   a measurement information collection terminal having installed therein sensors to acquire measurement information including sound information and video information on a three-dimensional work operation of a model worker during the simulated work of the work procedure, wherein the work procedure comprises a plurality of stages;
   a control unit having stored in a memory a plurality of control programs functioning as an evaluation criterion creation device that creates evaluation criterion information on the simulated work of the work procedure, based on the measurement information of the three-dimensional work operation of the model worker from the measurement information collection terminal; and
   a content creation device that creates and updates the training content, based on the measurement information of the three-dimensional work operation of the model worker, the evaluation criterion information and three-dimensional shape information of the work target device,
   wherein the evaluation criterion creation device detects a predetermined body motion of the model worker accompanying words and voices as a signal for entering a specific stage of the work procedure in which a know-how and method for avoiding risk possessed by the model worker appear,
   wherein upon detection of the predetermined body motion of the model worker to preset a required work time of the three-dimensional work operation the evaluation criterion creation device further detects a variation in voice information or video information or a variation in three-dimensional measurement information in the specific stage of the work procedure,
   wherein the evaluation criterion creation device creates the evaluation criterion information for each equally divided time during the required work time of the three-dimensional work operation in the specific stage of the work procedure based on the three-dimensional work operation of the model worker in the specific stage of the work procedure accompanying the variation in voice information or video information or the variation in three-dimensional measurement information in the specific stage of the work procedure, upon detection of the predetermined body motion of the model worker,
   wherein the evaluation criterion creation device monitors the three-dimensional work operation of the model worker in the specific stage as measurement information including a three-dimensional variation of a specific portion of interest of the model worker and time,
   wherein the evaluation criterion creation device updates the evaluation criterion information on the simulated work in the specific stage so as to evaluate the simulated work of the trainee in the specific stage of the work procedure by the evaluation criterion information updated when the predetermined body motion of the model worker is detected, and
   wherein the model worker and the trainee are different persons.

2. A content presentation system that presents training content based on three-dimensional shape of a work target device and a work procedure to a trainee, and has executed a simulated work in accordance with the work procedure in a simulated work space of virtual reality or augmented reality, the content presentation system comprising:
   a wearable terminal having stored in a memory a plurality of input and output programs functioning as content input sensors that input the training content including sound information, video information and three-dimensional shape information, and a content output device that outputs a signal of the training content to be transmitted and the training content to be presentable to the trainee;
   a control unit having stored in a memory a plurality of control programs functioning as an evaluation criterion creation device that acquires a three-dimensional work operation of the simulated work of a model worker as measurement information including sound information and video information during the simulated work of the work procedure, the work procedure comprising a plurality of stages, and detects a predetermined body motion of the model worker accompanying words and voices as a signal for entering a specific stage of the work procedure in which a know-how and method for avoiding risk possessed by the model worker appear, and further detects a variation in voice information or video information or a variation in three-dimensional measurement information upon detection of the predetermined body motion of the model worker to preset a required work time of the three-dimensional work operation, and creates evaluation criterion information for each equally divided time during the required work time of the three-dimensional work operation in the specific stage of the work procedure based on the three-dimensional work operation of the simulated work of the model worker in the specific stage of the work procedure accompanying the variation in voice information or video information or the variation in three-dimensional measurement information of the three-dimensional work operation of the simulated work of the model worker with respect to the three-dimensional shape in the specific stage of the work procedure, the control unit having stored in an additional memory a plurality of additional control programs functioning as a content creation device that creates and updates the training content, based on the measurement information of the three-dimensional work operation of the simulated work of the model worker, the evaluation criterion information and three-dimensional shape information of the work target device; and a training support server having a plurality of support programs stored therein and functioning as a work evaluation device that acquires the three-dimensional work operation in the simulated work of the trainee as measurement information based on the signal of the training content transmitted from the wearable terminal, evaluates the three-dimensional work operation of the trainee in the specific stage of the simulated work based on the evaluation criterion information, and outputs a result of the evaluation, wherein the evaluation criterion creation device monitors the model three-dimensional work operation of the simulated work of the model worker in the specific stage as measurement information including a three-dimensional variation of a specific portion of interest of the model worker and time, wherein the evaluation criterion creation device updates the evaluation criterion information on the simulated work in the specific stage so as to evaluate the simulated work of the trainee in the specific stage of the work procedure by the evaluation criterion information updated when the predetermined body motion of the model worker is detected, and wherein the model worker and the trainee are different persons.

3. The content creation system according to claim 1, wherein the measurement information collection terminal is composed of a wearable information terminal capable of presenting information to a worker who performs simulated maintenance work on a predetermined system or device to be maintained and managed.

4. The content creation system according to claim 3, wherein the wearable information terminal is a head mount display, and the predetermined body motion of the model worker includes a variation in line of sight of the model worker.

5. The content creation system according to claim 1, wherein the sensors comprise at least one of a three-dimensional camera, a motion sensor, a biometric sensor and a microphone.

6. The content creation system according to claim 1, wherein the control unit detects an additional predetermined body motion of the model worker as a signal for ending the specific stage of the work procedure at the time when the operation motion in the specific stage of the work procedure comes to an end.

7. The content creation system according to claim 1, wherein the sensors include first sensors capable of acquiring measurement information on the three-dimensional work operation, and a second sensor composed of a motion sensor or a biometric sensor and capable of detecting other body movements during the three-dimensional work operation.

8. The content presentation system according to claim 2, wherein the wearable terminal is capable of presenting information to the trainee who performs simulated maintenance work on a predetermined system or device to be maintained and managed.

9. The content presentation system according to claim 2, wherein the training support server requires for start the trainee to install necessary sensors to the wearable terminal so as to form the content input sensors of the wearable terminal.

10. The content presentation system according to claim 9, wherein the wearable terminal and the training support server further detect other body movements of the trainee by a motion sensor or/and a biometric sensor for each equally divided time during the required work time of the three-dimensional work operation in the specific stage of the work procedure.

11. The content presentation system according to claim 2, wherein the wearable terminal is a training support terminal capable of presenting training content from the training support server to the trainee, and which further comprises a measurement information collection terminal having model work sensors that acquire measurement information including sound information and video information on a three-dimensional work operation of the model worker during the simulated work of the work procedure, and the evaluation criterion creation device of the control unit acquires the measurement information from measurement information collection terminal.

* * * * *